United States Patent
Cronenberg et al.

(10) Patent No.: US 8,323,238 B2
(45) Date of Patent: Dec. 4, 2012

(54) MEDICAL INJECTOR WITH ROTATABLE BODY PORTIONS

(75) Inventors: Richard A. Cronenberg, Mahwah, NJ (US); Asif Fayyaz, Paramus, NJ (US); Atul Patel, Wilkes-Barre, PA (US); Lionel Vedrine, Palo Alto, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/063,829

(22) PCT Filed: Sep. 18, 2009

(86) PCT No.: PCT/US2009/057460
§ 371 (c)(1),
(2), (4) Date: Nov. 1, 2011

(87) PCT Pub. No.: WO2010/033790
PCT Pub. Date: Mar. 25, 2010

(65) Prior Publication Data
US 2012/0053516 A1    Mar. 1, 2012

Related U.S. Application Data

(60) Provisional application No. 61/192,389, filed on Sep. 18, 2008.

(51) Int. Cl.
*A61M 37/00* (2006.01)
(52) U.S. Cl. .................................................. 604/89
(58) Field of Classification Search .................. 604/82, 604/89, 90, 218, 223, 228, 229
See application file for complete search history.

(56) References Cited

U.S. PATENT DOCUMENTS

| 5,584,815 | A | 12/1996 | Pawelka et al. |
| 6,406,455 | B1* | 6/2002 | Willis et al. ................. 604/68 |
| 8,092,420 | B2* | 1/2012 | Bendek et al. ............... 604/89 |
| 2002/0095120 | A1 | 7/2002 | Larsen et al. |
| 2003/0149403 | A1 | 8/2003 | Barker et al. |
| 2011/0172640 | A1* | 7/2011 | Cronenberg et al. ......... 604/506 |
| 2011/0196310 | A1* | 8/2011 | Cronenberg ................. 604/189 |
| 2011/0201999 | A1* | 8/2011 | Cronenberg et al. .......... 604/89 |
| 2011/0202013 | A1* | 8/2011 | Jeter et al. ................... 604/228 |
| 2011/0213299 | A1* | 9/2011 | Cronenberg ................... 604/82 |
| 2011/0213315 | A1* | 9/2011 | Sweeney et al. ............. 604/208 |
| 2012/0041366 | A1* | 2/2012 | Fayyaz et al. ................. 604/89 |
| 2012/0041367 | A1* | 2/2012 | Cronenberg et al. .......... 604/89 |

FOREIGN PATENT DOCUMENTS

EP    0 630 663 A1    12/1994
WO    WO 2006058061 A1 *    6/2006

* cited by examiner

*Primary Examiner* — Nicholas Lucchesi
*Assistant Examiner* — Aarti B Berdichevsky
(74) *Attorney, Agent, or Firm* — Hoffman & Baron, LLP (57) ABSTRACT

A medical injector is provided herein which includes first and second body portions rotatably coupled together; a displaceable plunger disposed in at least one of the first and second body portions; a spring disposed to advance the plunger; and, a releasable retainer for retaining the plunger in a first portion against force of the spring. The releasable retainer releases the plunger upon a predetermined extent of relative rotation between the first and second body portions, thus allowing the spring to advance the plunger. Advantageously, the subject invention provides a medical injector having an automated plunger drive which is triggered upon rotation of injector body portions, thereby minimizing premature or failed activations.

4 Claims, 6 Drawing Sheets

MEDICAL INJECTOR WITH ROTATABLE BODY PORTIONS

FIELD OF THE INVENTION

This invention relates to medical injectors, and, more particularly, to medical injectors having plunger drive mechanisms.

BACKGROUND OF THE INVENTION

Medical injectors are well known in the prior art, including injectors which have internal drive mechanisms for plunger advancement. Plunger advancement may be utilized to conduct automated reconstitution of a two- or more part medicament and/or to cause automated injection. More specifically, the automation of plunger advancement may be utilized to cause combination of a multiple part (e.g., wet/dry) medicament. In addition, or alternatively, the automated advancement of the plunger may cause a needle to be advanced for injection and/or medicament to be driven through the needle during injection. Such automated action requires a trigger mechanism. Concerns exist over premature or failed trigger activation.

SUMMARY OF THE INVENTION

A medical injector is provided herein which includes first and second body portions rotatably coupled together; a displaceable plunger disposed in at least one of the first and second body portions; a spring disposed to advance the plunger; and, a releasable retainer for retaining the plunger in a first position against force of the spring. The releasable retainer releases the plunger upon a predetermined extent of relative rotation between the first and second body portions, thus allowing the spring to advance the plunger. Advantageously, the subject invention provides a medical injector having an automated plunger drive which is triggered upon rotation of injector body portions, thereby minimizing premature or failed activations.

These and other features of the subject invention will be better understood through a study of the following detailed description and accompanying drawings.

DETAILED DESCRIPTION OF THE INVENTION

With reference to the figures, a medical injector is shown and generally designated with the reference numeral 10. The medical injector 10 may be of various types, but preferably is of the pen injector type. The medical injector 10 may be used to administer various injectable liquids, particularly medicaments.

Figure 1:
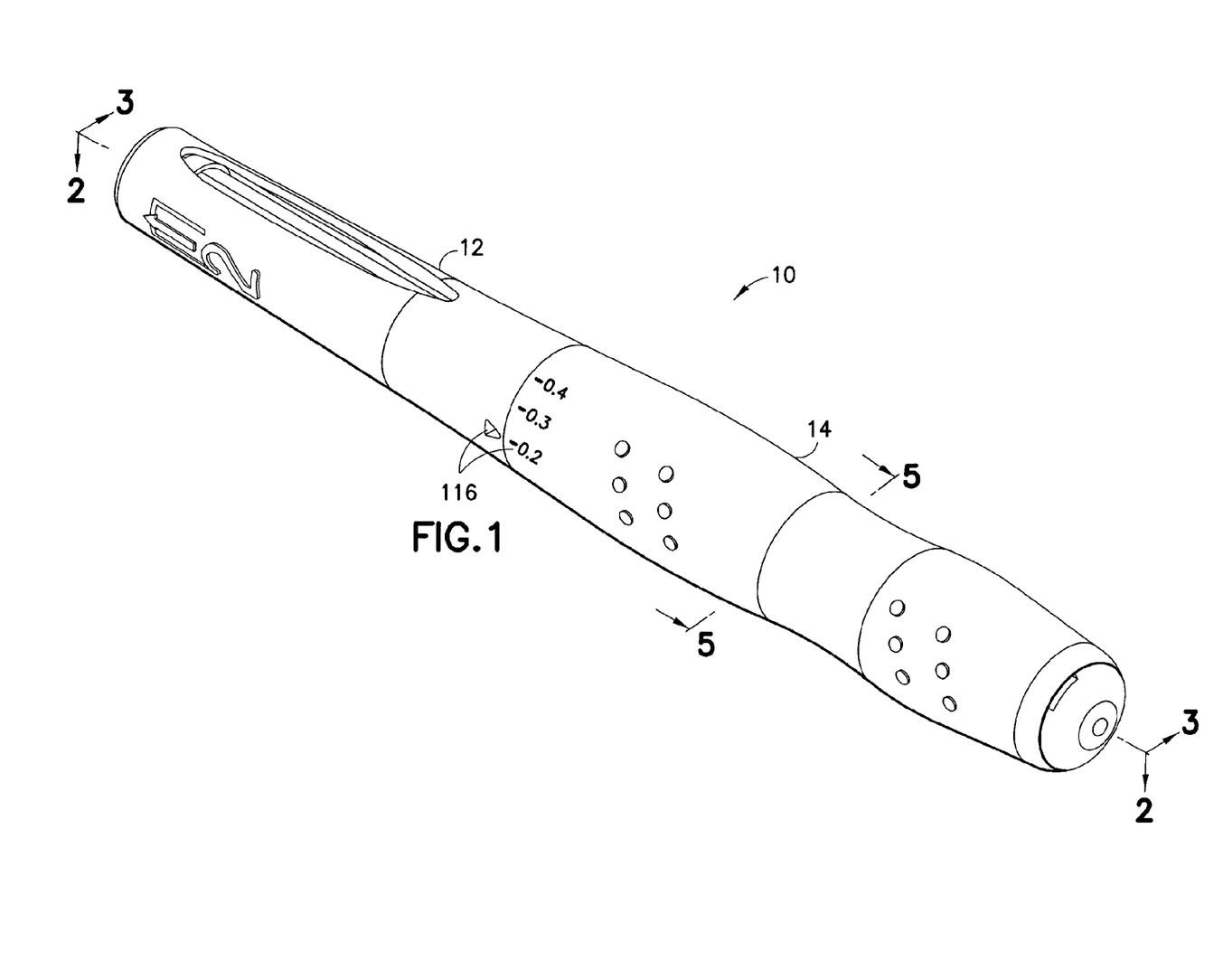
FIG. 1 is a perspective view of a medical injector formed in accordance with the subject invention.

With reference to FIG. 1, the medical injector 10 includes rotatably coupled first and second body portions 12, 14. The first and second body portions 12, 14 are complementarily formed so as to allow relative rotation therebetween, by movement of one or both of the components.

Figure 2:
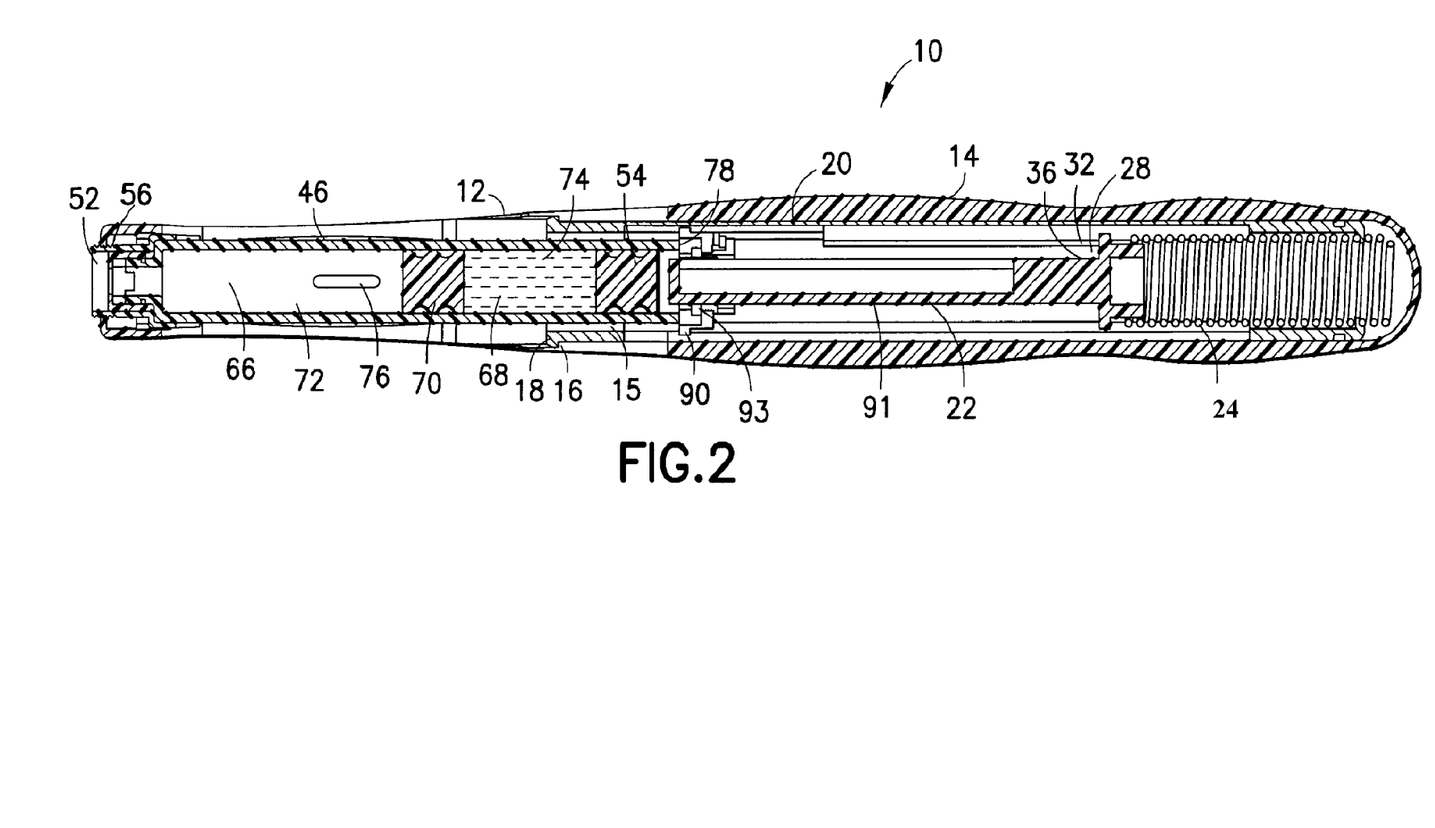
FIG. 2 is a cross-sectional view taken along line 2-2 of FIG. 1.

The first and second body portions 12, 14 are preferably formed of rigid material and to varying extents accommodate different portions of the medical injector 10. Preferably, to obtain rotatability, as shown in FIG. 2, a track 16 is formed in one of the first and second body portions 12, 14, with one or more detents 18, formed opposite the track 16, being seated in the track 16 so as to lock the first and second body portions 12, 14 together once assembled. The detents 18 may be formed slidable along the track 16 so as to permit the first and second body portions 12, 14 to rotate relative to one another. One or more stops 15 may be located along the track 16 to limit the extent of relative rotation.

Figure 3:
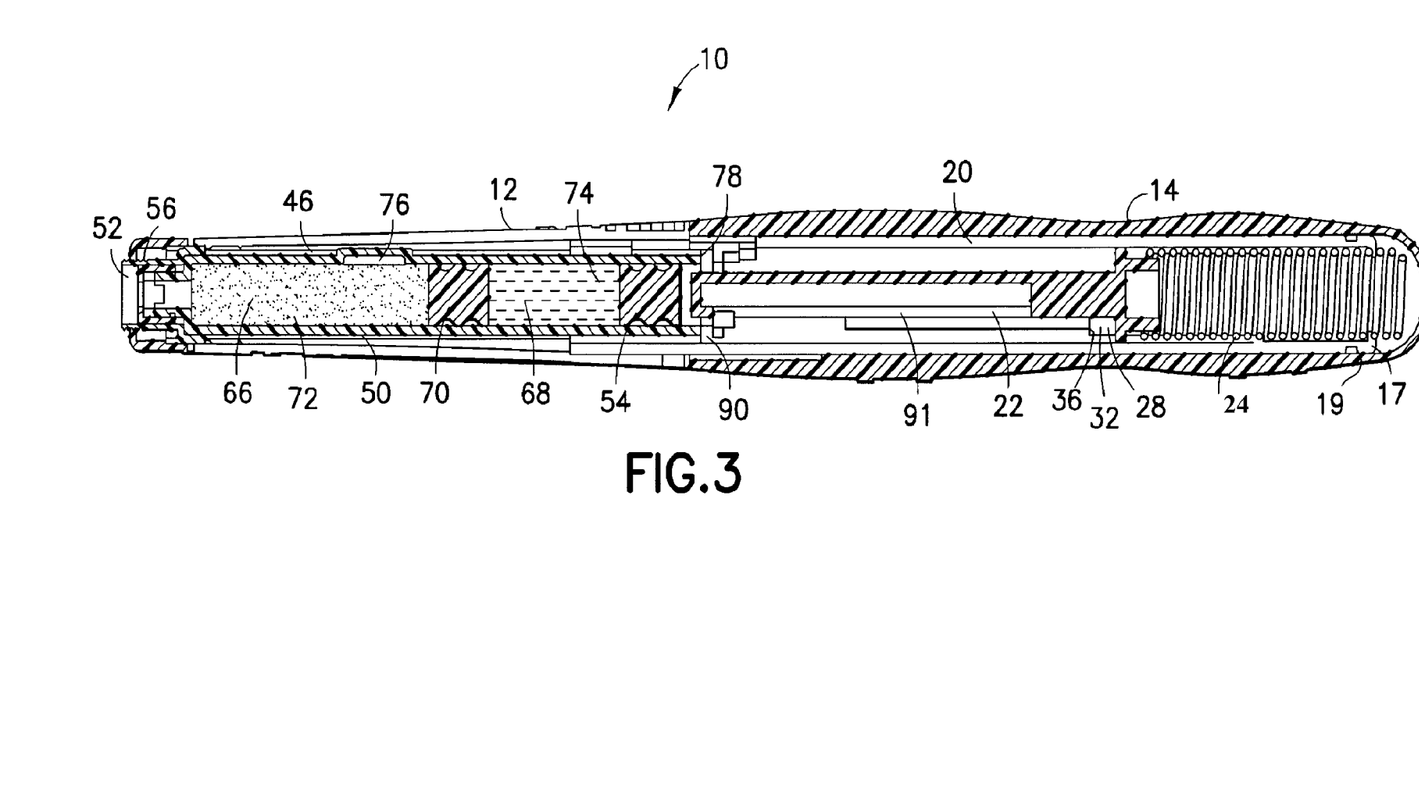
FIG. 3 is a cross-sectional view taken along line 3-3 of FIG. 1.
Figure 4:
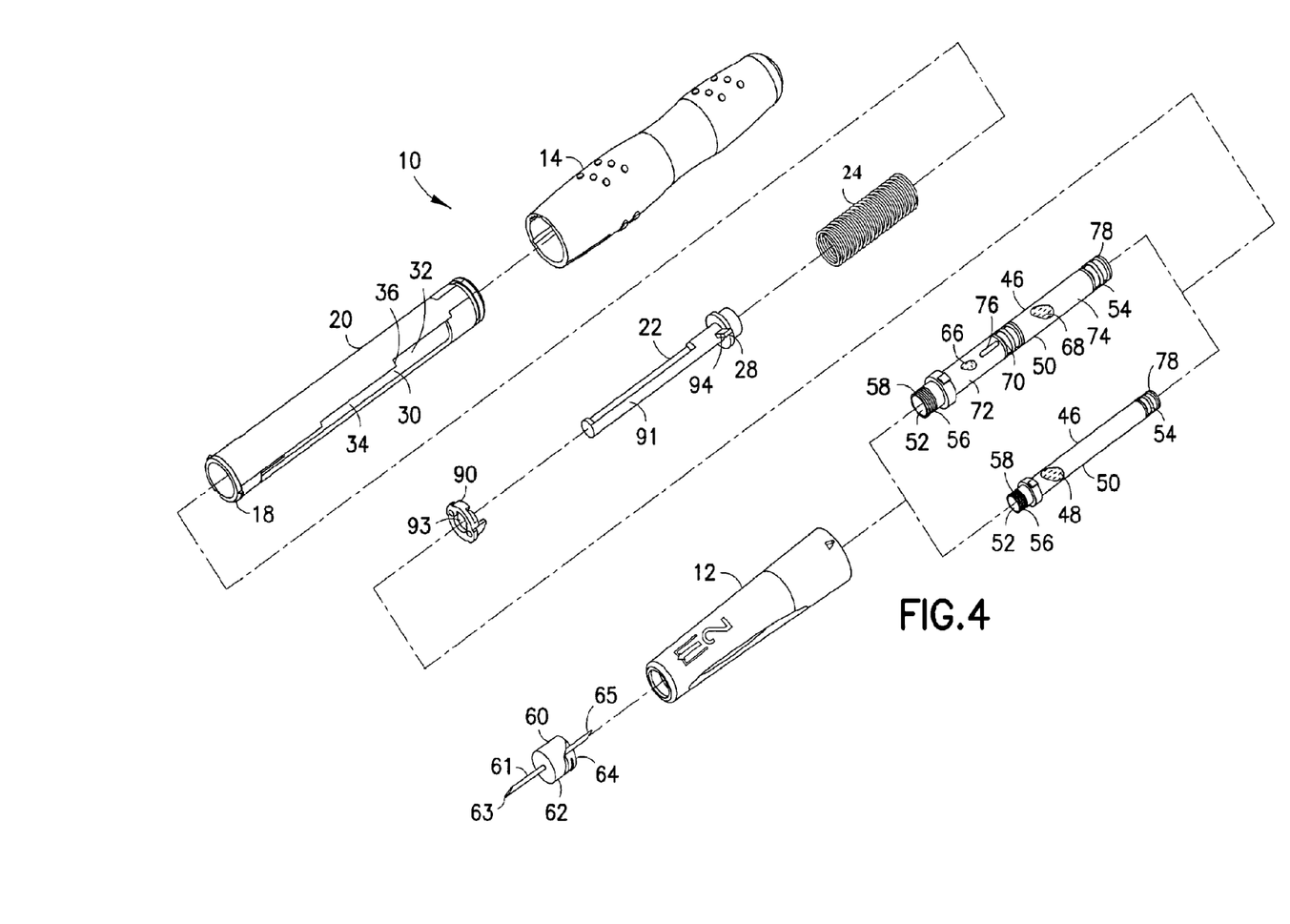
FIG. 4 is an exploded view of a medical injector formed in accordance with the subject invention.

In a preferred arrangement, with reference to FIGS. 2-4, the second body portion 14 may include an interior sleeve 20 on which the detents 18 are formed. It is preferred the interior sleeve 20 be non-rotatably coupled to the first body portion 12. The stops 15 may be provided on the first body portion 12 to prevent rotation. In addition, it is preferred that the interior sleeve 18 be coupled to the second body portion 14 in any known manner so as to permit rotation of the second body portion 14 thereabout such as through mating snap fingers 17 and engagement surface 19. With the interior sleeve 18 being non-rotatably coupled to the first body portion 12, the interior sleeve 18 is held fixed with the second body portion 14 being rotatable thereabout. Alternatively, the detents 18 may be formed directly on the second body portion 14.

The medical injector 10 includes an axially-displaceable plunger 22. The plunger 22 may be formed as a single piece or modular components. The modular components may be fixed to one another or located adjacently, but not connected, so as to move together. In a preferred embodiment, at least a majority, if not the entirety, of the plunger 22 is initially located in the second body portion 14. A spring 24 is also provided configured and positioned to advance the plunger 22 a predetermined distance. Preferably, the spring 24 is a compression or coil spring, but other biasing elements may likewise be utilized. Preferably, the spring 24 is positioned in the second body portion 14.

A releasable retainer 26 is provided configured and positioned to releasably retain the plunger 22 in an initial first state against the force of the spring 24. The releasable retainer 26 is configured such that, upon a predetermined extent of relative rotation between the first and second body portions 12, 14, the releasable retainer 26 releases the plunger 22 thereby allowing the spring 24 to advance the plunger 22 the predetermined distance. As will be appreciated by those skilled in the art, various releasable retainers may be used with the subject invention.

It is preferred that the plunger 22 be advanced in a distal direction. As used herein, distal refers to a direction towards a patient during use, while proximal refers to a direction away from a patient during use.

Figure 5:
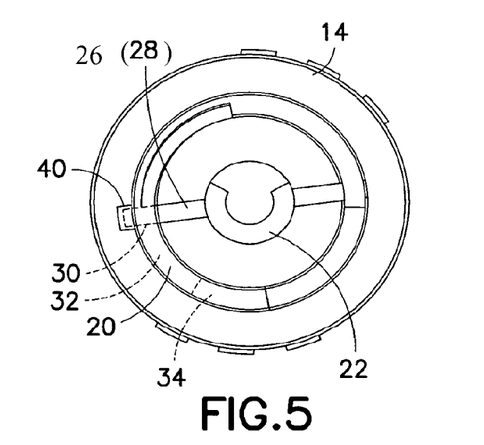
FIG. 5 is a cross-sectional view taken along line 5-5 of FIG. 1.

By way of non-limiting example, the releasable retainer 26 may be one or more latches 28 formed on the plunger 22, as shown in FIGS. 2, 3 and 5. One or more channels 30 are formed radially outwardly of the plunger 22 with each having a first portion 32, that is disposed transversely to the plunger 22, and a second portion 34, that is disposed generally parallel to the plunger 22. The number of the channels 30 corresponds to the number of the latches 28. The channels 30 are formed to accommodate the latches 28. The channels 30 are formed in the interior sleeve 20 and/or the second body portion 14.

In an initial state, the latches 28 are located in the first portions 32 of the channels 30, as shown in FIGS. 2 and 3. The interengagement of the latches 28 with ledges 36 defined adjacent to the first portions 32 of the channels 30 retains the plunger 22 in the first position against force of movement of the spring 24. To release the plunger 22, the latches 28 are displaced out of the first portions 32 of the channels 30 and into the second portions 34 of the channels 30. In the second portions 34, the latches 28 are free to translate the second portions 34, and thus the spring 24 causes distal advancement of the plunger 22.

The latches 28 may be caused to be displaced from the first portions of the channels 30 in various manners. Preferably, one of the channels 30 is formed in the interior sleeve 20 so as to extend through the interior sleeve 20. As shown in FIG. 5, one of the latches 28 protrudes from the plunger 22 and through the interior sleeve 20, e.g., via the channel 30, so as to protrude from the interior sleeve 20. A slot 40, or other engaging member, may be formed and located on the second body portion 14 to engage the latch 28. With rotation of the second body portion 14, the latch 28 may be caused to rotate, thus causing rotation of the plunger 22, and, thus, displacement of the latch 28 into the second portion 34 of the channel 30.

The medical injector 10 includes a reservoir 46 disposed in the first body portion 12 formed to accommodate medicament or other substance 48 for injection into a patient. As shown in FIG. 4, the reservoir 46 may be a single chamber disposed in a barrel 50 sealed at a proximal end by a septum 52 and sealed at a distal end by a stopper 54 which is formed to be slidable through the barrel 50 for urging the substance 48 therefrom, as known in the art. The medical injector 10 also includes a needle mounting surface 56 having features 58 formed thereon for mounting a needle 60 thereto. The needle 60 may include a hub 62 having mounting features 64 provided thereon for cooperative engagement with the features 58 in mounting the needle 60 to the needle mounting surface 56. The features 58 and the mounting features 64 may be of any known cooperating elements which permit a mechanical connection therebetween, such as threads or bayonet lock, and/or a frictional interengagement, such as a Luer mounting. The needle mounting surface 56 may be formed on the first body portion 12 or a component thereof, such as a needle adaptor fixed to the reservoir 46.

The needle 60 also includes a needle cannula 61 having a distal end 63, formed for insertion into a patient, and a proximal end 65.

The reservoir 46 may be configured to accommodate multiple components which are mixable for reconstitution. For example, as shown in FIG. 4, the reservoir 46 may accommodate first and second mixable components 66, 68. The stopper 54 may be associated with the reservoir 46 such that distal advancement of the stopper 54 over a predetermined distance shall cause mixing of the first and second mixable components 66, 68. Any known arrangement for allowing such mixing may be utilized. By way of non-limiting example, the first and second mixable components 66, 68 may be separated by a secondary stopper 70. The secondary stopper 70 divides the reservoir 46 into first and second chambers 72, 74, respectively, accommodating the first and second mixable components 66, 68. The septum 52 seals off the distal end of the first chamber 72, while the stopper 54 is positioned to seal off the proximal end of the second chamber 74. Preferably, if a dry component is used as one of the mixable components, the dry mixable component is located in the first chamber 72.

One or more by-pass channels 76 are formed in the wall of the reservoir 46. In an initial state, as shown in FIG. 4, the secondary stopper 70 is located at least partially proximally of the by-pass channels 76 so as to define a seal between the first and second chambers 72, 74 and to define a seal between the second chamber 74 and the by-pass channels 76. With distal advancement of the stopper 54, and with the second mixable component 68 being wet and generally incompressible, force of movement of the stopper 54 is transmitted to the secondary stopper 70 through the second mixable component 68. With sufficient distal movement of the secondary stopper 70, the second chamber 74 comes into communication with the by-pass channels 76, thus allowing the second mixable component 68 to be urged into the first chamber 72 with further distal movement of the stopper 54. With sufficient distal advancement of the stopper 54, the second chamber 74 is collapsed with none or substantially none of the second mixable component 68 remaining therein. In addition, the secondary stopper 70 is located so as to define a seal between the first chamber 72 and the by-pass channels 76. The first and second mixable components 66, 68 are mixed within the first chamber 72, such as through agitation of the medical injector 10, so as to produce the injectable substance 48, ready for injection.

The barrel 50 of the reservoir 46 may be the barrel of a separate drug cartridge, as shown in the figures, or a portion of the medical injector 10, particularly the first body portion 12.

As will be recognized by those skilled in the art, other arrangements for permitting reconstitution may be utilized. In addition, more than two-part systems, such as three-part and so forth, systems may be utilized. Active medical ingredients may be included in one or both of the first and second mixable components 66, 68. The first mixable component 66 may be dry (e.g., a powder or granular substance) and/or a liquid (e.g., flowable (slurry or liquid)). As mentioned above, the second mixable component 70 is preferably only a wet flowable component, such as a liquid or slurry.

Distal advancement of the plunger 22 under force of the spring 24 may be used to achieve one or more objectives. The plunger 22 is configured to act against the stopper 54 and cause displacement thereof. With the reservoir 46 being configured for reconstitution, autoreconstitution of the contents of the reservoir 46 may be achieved. In addition, or alternatively, the medical injector 10 may be configured to be an autoinjector, where the needle 60 is initially housed within the first body portion 12 and forced thereout of under force of the spring 24 so as to pierce a patient's skin, e.g., with forward movement of the reservoir 46, as known in the art. In addition, or alternatively, distal advancement of the plunger 22 may cause administration of the contents of the reservoir 46 through the injected needle.

Depending on the desired effect, the medical injector 10 may be configured to have the plunger 22 be driven a predetermined distance. A physical stop, such as interengagement between a portion of the plunger 22 and a proximal end 78 of the reservoir 46 (e.g., proximal end of the barrel 50), may be employed to limit distal advancement of the plunger 22. Under certain circumstances, the plunger 22 may be distally advanced without the needle 60 being mounted to the medical injector 10. Thus, the reservoir 46 is not vented during such action. With the needle 60 being subsequently mounted to the reservoir 46, any residual gases trapped in the reservoir 46 are purged through the needle 60. It may be preferred to not provide a physical stop to the distal advancement of the plunger 22. In this manner, the contents of the reservoir 46 may be maximally compressed under force of the spring 24. With subsequent mounting of the needle 60 onto the medical injector 10, the reservoir 46 is vented thus permitting further distal advancement of the plunger 22. This secondary distal advancement may assist in priming the needle 60 for use.

The medical injector 10 may be a fixed dose injector configured to administer single or multiple fixed doses. In addition, the medical injector 10 may be configured to permit dose setting for either a single or multiple doses. In a preferred embodiment, the medical injector 10 is a single, variable-dose autoreconstitution injector.

As will be appreciated by those skilled in the art, various configurations to permit dose setting may be utilized. By way of non-limiting example, and with reference to the figures, a dose ring 90 may be provided with a plurality of axially and radially spaced-apart abutment surfaces 92.

The abutment surfaces 92 are axially alignable with an engagement surface 94 formed on the plunger 22 such that with sufficient distal displacement of the plunger 22 at least one of the abutment surfaces 92 will be caused to be engaged by the engagement surface 94 thus limiting the stroke of the plunger 22. The engagement surface 94 may be defined on one or more of the latch tabs 28. With this arrangement, a controlled amount of distal displacement of the plunger 22 may be transmitted to the stopper 54. Stem 91 of the plunger 22 passes through opening 93 of the dose ring 90 to obtain proper alignment of the engagement surface 94 with the corresponding abutment surface 92 and so that the stem 91 may engage the stopper 54. Moreover, stroke length corresponding to the movement of the plunger 22 may be adjusted depending on the abutment surface 92 which is in engagement with the engagement surface 94. The greater the initial distance of the abutment surfaces 92 from the engagement surface 94, the corresponding greater dose that will be caused to be administered. Regardless of the selected dose amount, it is preferred that the plunger 22 having a fixed length of stroke for distal displacement during administration of an injection. The further abutment surfaces 92 have greater distal movement of the plunger 22. The extent of movement of the plunger 22 dictates the extent of movement of the stopper 54 and, thus, dictates the amount of the injectable solution 48 to be driven from the reservoir 46 in an injected dose. The dose ring 90 is preferably stationary. A spring arm 120 may extend from the dose ring 90 to resiliently press against the plunger 22 and provide stability thereto.

Figure 6:
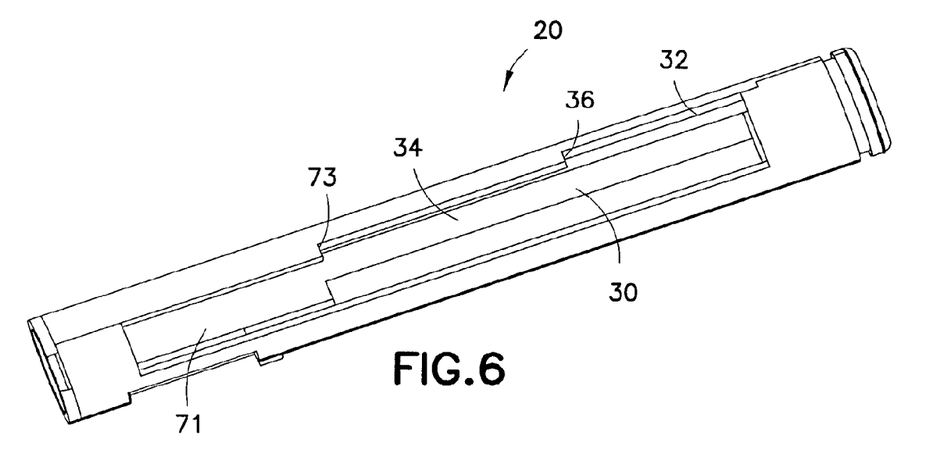
FIG. 6 is a cross-sectional view of an interior sleeve useable with the subject invention.
Figure 7:
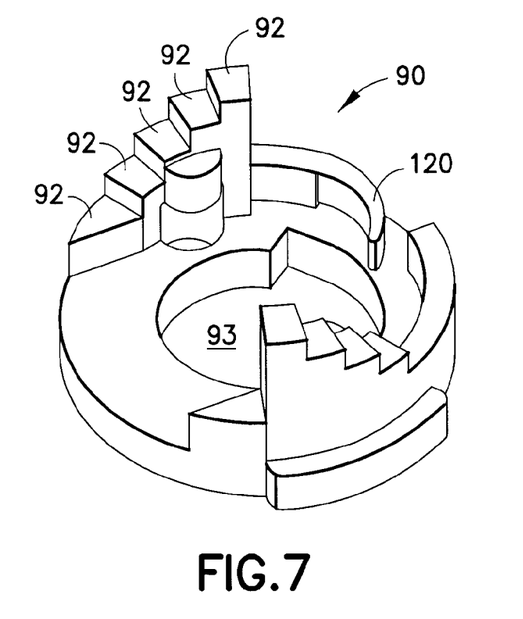
FIG. 7 is a perspective view of a dose ring useable with the subject invention; and, FIG. 8 is a schematic showing an arrangement for restricting radial motion.

The dose is selected by rotating the second body portion 14 which is fixed to the plunger 22 so as to rotate therewith. To prevent the second body portion 14 from setting a dose prior to proper preparation of the medical injector 10, such as prior to mixing of the mixable components 66, 68, rotation of the plunger 22 may be limited by interengagement of the latch 28 with the channel 30. As shown in FIG. 6, open space 71 may be defined at the distal terminus of the second portion 34 of the channel 30 which extends radially to permit rotation of the latch 28 thereinto. In this manner, doses can be adjusted by rotating the plunger 22 to axially locate the engagement surface 94 with a desired of the abutment surfaces 92. The channel 30 may be formed with one or more catches 73 which initially catch the latch 28 upon distally advancing the second portion 34 of the channel 30. By permitting such radial adjustment at the terminus of the channels 30, dose setting may be restricted to post-advancement of the plunger 22. Optionally, the channel 30, particularly at the second portion 34, may be made with sufficient radial width to permit dose setting. Thus, dose setting can be achieved at any instance at the initiation of, during, or after advancement of the plunger 22.

Figure 8:
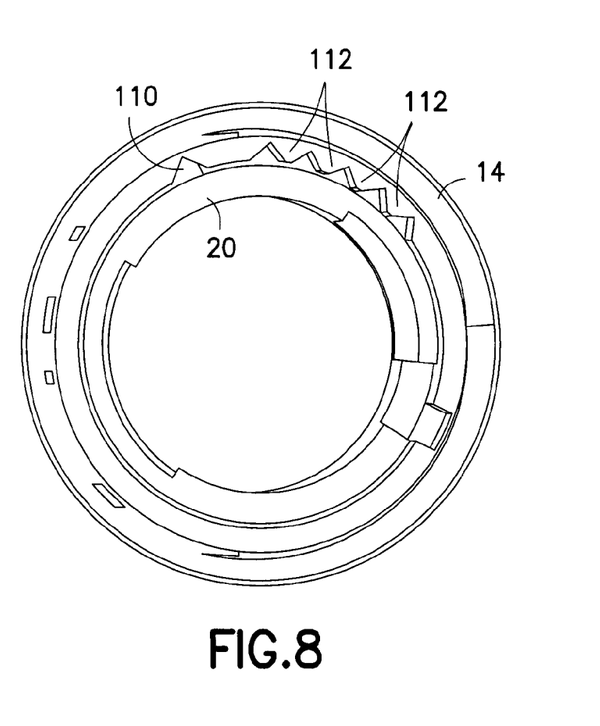

It is preferred that the second body portion 14 be releasably retained in positions corresponding to the various dose settings. In this manner, it is preferred that once a dose has been set, there is no inadvertent rotation of the second body portion 14, thus avoiding that an improper of the abutment surfaces 92 engage the engagement surface 94. Such an arrangement is disclosed in U.S. Pat. No. 6,793,646. As shown in U.S. Pat. No. 6,793,646, with reference to FIG. 8, one or more tabs 110 may be formed on the interior sleeve 20 which are selectively engageable with one or more ratchet teeth 112 formed on the second body portion 14. The ratchet teeth 112 may be circumferentially spaced apart and positioned to represent dose settings corresponding to the abutment surfaces 92. The tabs 110 nest in between the ratchet teeth 112 at given radial positions of the plunger 22 corresponding to different dose sizes. With turning of the second body portion 14, the tabs 110 are caused to by-pass the ratchet teeth 112. The ratchet teeth 112 maintain the radial position of the second body portion 14.

In addition, it is preferred that the plunger 22 be limited in axial movement so as to permit a fixed stroke length of distal advancement for dose administration. The stroke of an injection is defined by the extent of distal movement of the plunger 22. The plunger 22 may be advanced in any known manner for injection, including under force of movement of the spring 24.

Indicia 116 may be provided to represent doses. The indicia 116 may include numeral representations and a pointer or other indicator. The indicia 116 may be on both the first and second body portions 12, 14 to provide dose indications.

What is claimed is:

1. A medical injector comprising:
   first and second body portions rotatably coupled together;
   a displaceable plunger disposed in at least one of said first and second body portions;
   a spring disposed to advance said plunger;
   a reservoir accommodating first and second mixable components, said first and second mixable components being mixed with advancement of said plunger; and
   a releasable retainer for retaining said plunger in a first position and in a second position against force of said spring, wherein said releasable retainer includes at least one latch tab and at least one channel, said channel having a first portion disposed transversely to said plunger, a second portion that is disposed generally parallel to said plunger, a third portion disposed transversely to said plunger, and a fourth portion that is disposed generally parallel to said plunger, said second portion extending between said first and third portions, said fourth portion extending from said third portion, said latch tab being disposed in said first portion causing said plunger to be retained in said first position, said latch tab being disposed in said third position causing said plunger to be retained in said second position,
   wherein, said releasable retainer releases said plunger upon a predetermined extent of relative rotation between said first and second body portions with displacement of said latch tab from said first portion to said second portion of said channel, thus allowing said spring to advance said plunger from said first position to said second position to mix said mixable components, and
   wherein, with said plunger in said second position, said releasable retainer releases said plunger upon a predetermined extent of relative rotation between said first and second body portions with displacement of said latch tab from said third s portion to said fourth s portion of said channel, thus allowing said spring to further advance said plunger.

2. A medical injector as in claim 1, further comprising means for releasably retaining said first body portion in predetermined rotational positions relative to said second body portion.

3. A medical injector as in claim 1, further comprising a dose ring including a plurality of axially and radially spaced-apart abutment surfaces, said abutment surfaces being selectively axially alignable with said latch tab.

4. A medical injector as in claim 3, wherein said abutment surfaces are selectively axially alignable with said plunger in said second position.

* * * * *